United States Patent [19]
Brown et al.

[11] Patent Number: 4,711,482
[45] Date of Patent: Dec. 8, 1987

[54] REACHING AID FOR THE HANDICAPPED

[75] Inventors: Larry D. Brown; Kevin D. Brown, both of Sayre, Pa.

[73] Assignee: N/C Industries, Sayre, Pa.

[21] Appl. No.: 17,994

[22] Filed: Feb. 24, 1987

[51] Int. Cl.4 .............................................. B25J 1/04
[52] U.S. Cl. .................................................. 294/19.1
[58] Field of Search ..................... 294/11, 19.1, 22–24, 294/50.8, 88, 100, 104, 115, 106; 135/65, 66, 75, DIG. 11

[56] References Cited
U.S. PATENT DOCUMENTS

| | | | |
|---|---|---|---|
| 465,222 | 12/1891 | Ulbricht | 294/19.1 |
| 2,646,304 | 7/1953 | Chadwick | 294/19.1 |
| 3,534,993 | 10/1970 | Le Vesque | 294/19.1 X |
| 3,591,226 | 7/1971 | Elmore et al. | 294/19.1 |
| 4,231,603 | 11/1980 | van Zelm | 294/19.1 |
| 4,441,746 | 4/1984 | Corboy | 294/19.1 X |
| 4,527,824 | 7/1985 | Rosenfeld | 294/19.1 X |

Primary Examiner—Johnny D. Cherry
Attorney, Agent, or Firm—Ralph R. Barnard

[57] ABSTRACT

A reaching aid for handicapped or elderly people which is built into a rod or cane having a pair of jaws at one end. The jaws are actuated by a small electric motor concealed in the rod, and controlled by a switch in the handle of the cane. The rod may be telescoping to allow for adjustment of length.

7 Claims, 5 Drawing Figures

REACHING AID FOR THE HANDICAPPED

BACKGROUND OF THE INVENTION

The invention pertains to the field of aids for the handicapped. More particularly, the invention pertains to devices to help handicapped people to pick up small items which are otherwise out of reach.

It is a major problem for the aged or handicapped to pick up objects which are out of reach, whether on the floor or on a shelf. Many elderly or handicapped people are confined to wheelchairs or in bed and cannot move sufficiently to reach objects even on their own level. Often they lack sufficient strength in their hands to properly grip an item, even if they could pick it up otherwise.

There have been many attempts at reaching aids for the handicapped and other similar applications in the prior art. Also common in the prior art are the shelf reachers used in grocery stores to reach cans on high shelves. Those of which I am aware which have been patented are the following:

| Inventor | U.S. Pat. No. | Date |
| --- | --- | --- |
| Ulbricht | 465,222 | 1891 |
| Mason | 2,346,038 | 1944 |
| Sisson | 3,093,402 | 1963 |
| Hollis | 3,425,734 | 1969 |
| Elmore | 3,591,226 | 1971 |
| Smith | 4,200,322 | 1980 |
| Van Zelm | 4,231,603 | 1980 |
| Van Zelm | 4,374,600 | 1983 |
| Corboy | 4,441,746 | 1984 |
| Rosenfield | 4,527,824 | 1985 |

All of the above, except Rosenfeld, are manual mechanical aids, often combined with a cane or other support. These devices present major problems for the frail elderly, who often cannot exert enough gripping force to close a mechanical gripper, or hold a grip long enough to retrieve the object, if they could exert a large enough initial force.

It is thus an object of the invention to present a gripping and reaching aid for the handicapped which does not require any physical effort to establish or hold a grip.

Rosenfeld is an electric device using a small fan to create a vacuum at the end of cane. While this might work to pick up especially light flat objects such as single sheets of paper, it would be impractical for anything of even minor weight or roughness.

It is a further object of the invention to provide a reaching aid which is capable of lifting objects of irregular shape and more than negligable weight.

SUMMARY OF THE INVENTION

The invention presents a reaching aid for handicapped or elderly people which is built into a telescoping rod or cane having a pair of jaws at one end. The jaws are actuated by a small electric motor concealed in the rod, and controlled by a switch in the handle of the cane.

DESCRIPTION OF THE PREFERRED EMBODIMENT

In the various figures, identical numbers refer to identical elements. Where there are two identical elements in a single drawing, the individual elements are numbered the same (i.e. "6") and may be distinguished by appended letters ("6a", "6b") if necessary.

Figure 1:
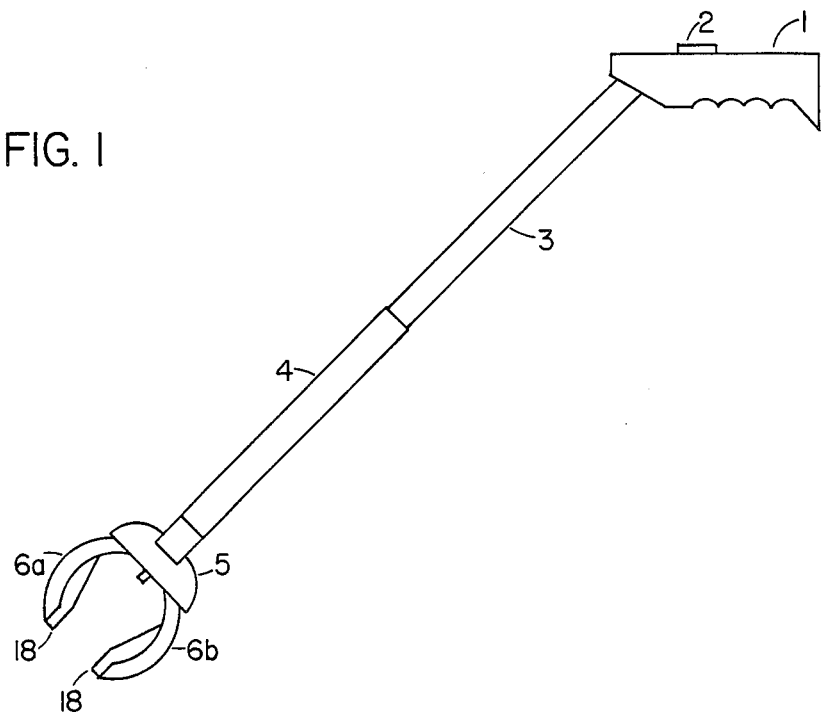
FIG. 1 shows an overall view of the invention

FIG. 1 shows an overall view of the reaching aid. A handle (1) is shaped to fit the hand of the user, much like a wheelchair- or bicycle-handle grip. The body of the aid may be one piece, but preferably is made up of two parts (3) and (4), of slightly different sizes so as to form a telescoping unit. The length of the aid may thus be adjusted by sliding elements (3) and (4) relative to each other. Such a telescoping length would be difficult or impossible in the prior art mechanical reaching aids, but is no problem in this invention. A length of approximately 28" to 40" is preferred, although other lengths are certainly possible. The body is preferably made of plastic, such as PVC pipe, to minimize the possibility of electrical shock. Other materials are, of course, possible.

The handle (1) and body (3,4) preferably meet at an angle, so as to allow the user to hold the handle at a comfortable angle while still being able to reach the floor with the aid.

At the end of the aid are two jaws (6a, 6b). The jaws can be moved relative to each other to grip and release objects. The inside of the jaws (6a, 6b) is preferably covered with a soft sponge pad (18) to allow the maximum in gripping ability. Preferably, the jaws open to at least two inches, to allow the user to pick up pill bottles, telephone handsets or the like.

Figure 3A:
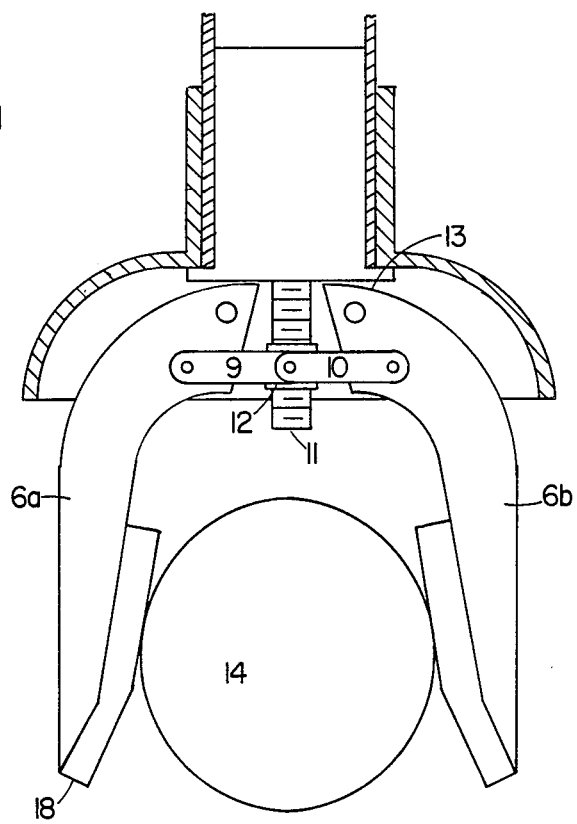
FIGS. 3a and 3b show a close-up of the jaw mechanism of the invention
Figure 3B:
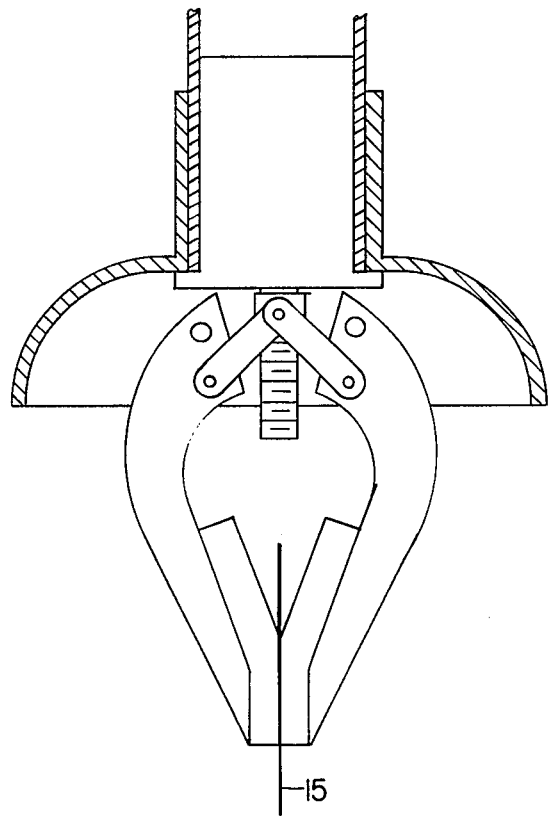

The preferred embodiment of the invention has two angled sections to the gripping surfaces of the jaws, as can best be seen in FIGS. 3a and 3b. The section (16) at the end of the jaws is arranged so that the sections on the two jaws (6a),(6b) are parallel when the jaws are closed. Thus, a large area is provided to grip thin materials such as papers (15) (FIG. 3b). The section (17) of the jaws nearest the pivots is arranged so as to be nearly parallel when the jaws are open, thus providing maximum gripping area for larger objects such as pill bottles (14) (FIG. 3a) or the like.

Figure 2:
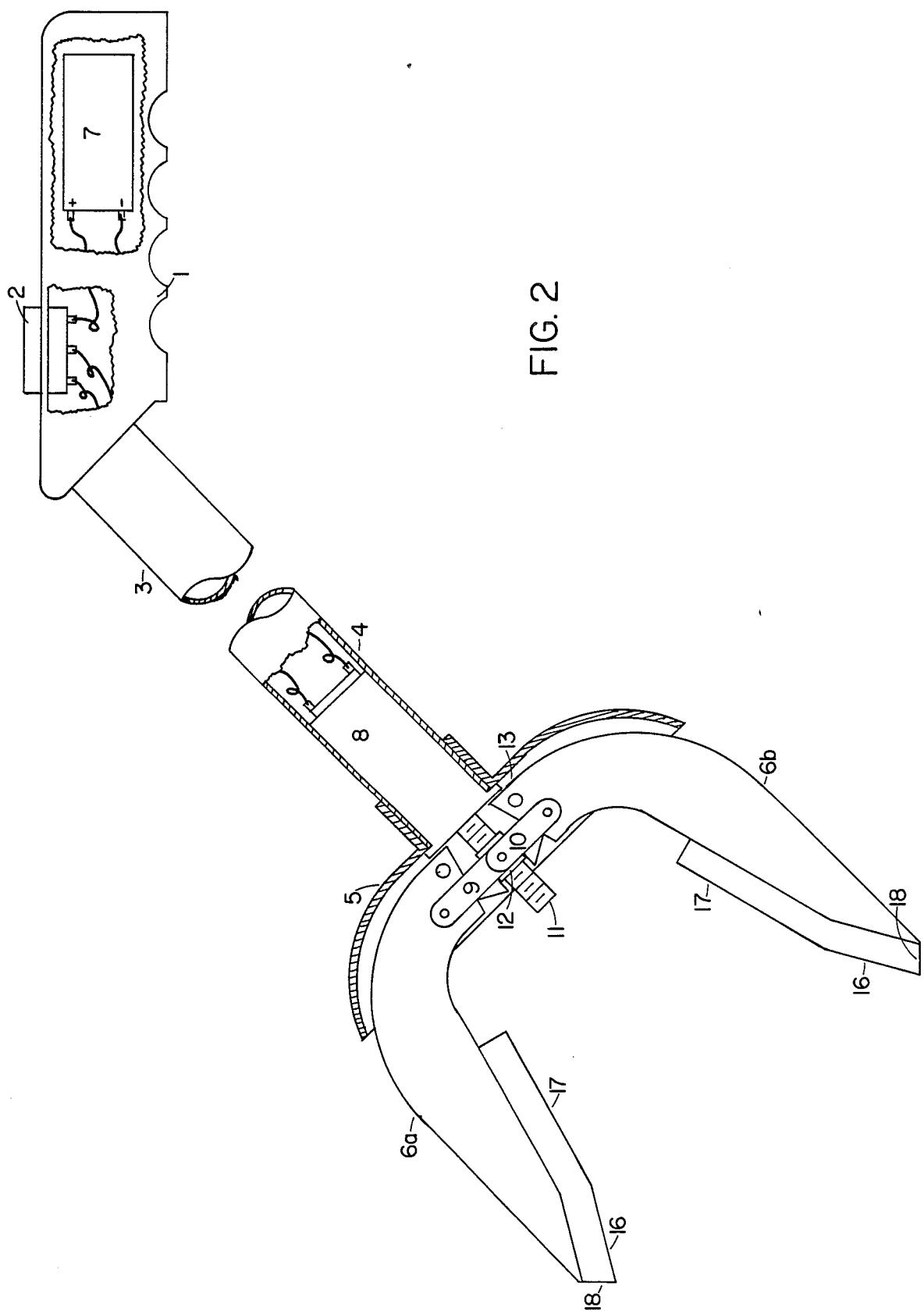
FIG. 2 shows a cutaway view of the invention

FIGS. 3a and 3b show details of the preferred embodiment of the jaw assembly. The two jaws (6a, 6b) are pivoted close to their ends on a pivot block (13). The jaws (6a, 6b) are attached to each other by a toggle having links (9) and (10). Each link is attached at one end to a jaw (6a, 6b) and at the other and to the other link and a threaded block (12). Engaging with the threaded block (12) is the threaded rotating shaft (11) of a small electric motor (8) FIG. 2,). As can be seen in FIGS. 3a and 3b, as the motor shaft turns the threaded block is drawn upwards toward the motor. The toggle causes the jaws to close progressively as the threaded block approaches the motor, until the jaws are fully closed (FIG. 3b). The motor will tend to stall out when an object is tightly gripped, and will not release when the power is removed. To release an object held by the jaws it is necessary to run the motor in the other direction, causing the threaded block to move away from the body of the reaching aid, moving the toggle arms outward, which in turn opens the jaws. Thus, the user will not drop the gripped object as he retrieves it, and no sustained hand grip is required.

The battery (7) for the motor (8) is most conveniently located in the handle (1), which is easily made large enough to accommodate it. A 9 volt "transistor radio" type has been found to be adequate, or a series of "AA", "C" or "D" cylindrical flashlight batteries could be used. The motor (8) is any DC type small enough to fit in the body (4) and of appropriate voltage requirements for the batteries used.

Figure 4:
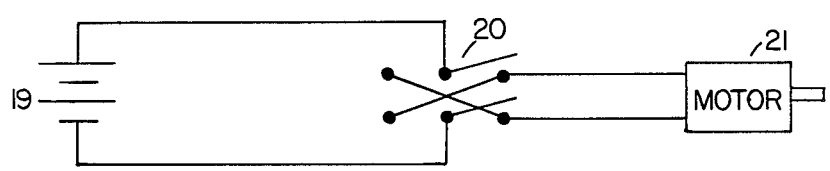
FIG. 4 shows a schematic of the wiring of the invention

The aid is controlled by a control circuit. As can be seen from FIG. 4, the preferred embodiment of the circuit uses a simple double pole double throw switch (20) arranged to run the DC motor (21) in a preselected direction as the switch is held in one position or the other by reversing the leads from the battery (19). Preferably switch (20) is of the center-off spring-loaded kind, so that releasing the switch will remove power from the motor. Alternatively, the circuit could be made more complex, detecting the current surge as the motor stalls out and stopping the current automatically.

The switch (2) is preferably mounted either on top of the handle (1), as shown, or underneath the handle similar to a vacuum cleaner switch. Alternatively, two pushbutton switches could be used in place of the single DPDT toggle or slide switch shown.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

I claim:
1. A reaching aid for the handicapped, comprising:
   a. a hollow body having two ends and a length therebetween at least sufficient for a seated person holding the body to reach the floor without bending;
   b. a handle located on one end of the body;
   c. gripper means for holding objects, located on the opposite end of the body from the handle, comprising:
      1. pivot block means attached to the end of the body;
      2. two jaw means each having a pivot end and a gripping end and an arm therebetween;
      3. the jaw means being pivotally attached to the pivot block means at the pivot end, whereby the jaw means as a pair may pivot on the pivot block means from a closed position wherein the gripping ends of the jaw means touch to an open position wherein the gripping ends are separated;
      4. toggle means for driving the jaw means between the open and closed positions, comprising two toggle links each having two ends and a length therebetween, each toggle link being pivotally attached to a jaw means at one end, the point of attachment being on the arm of the jaw means near the pivot end, and being pivotally attached to the other toggle link at the other end;
      5. the lengths of the toggle links being chosen such that when the lengths of the toggle links are aligned with each other the jaw means are in the open position, and when the ends of the toggle links which are attached to each other are drawn toward the pivot block means the jaw means are drawn into the closed position;
      6. threaded block means pivotally attached to the two toggle links at the end of the links where they are attached to each other, having a central bore adapted to receiving a rotating motor shaft;
   d. electric motor means having a driven rotating shaft output and an electrical input, whereby electrical power applied to the electrical input will cause the shaft to rotate in a selected direction, the motor means being located in the end of the body next to the pivot block means, with the shaft penetrating the pivot block means between the points of attachment of the jaw means;
   e. the shaft of the motor means being threaded, and of sufficient length, diameter, and threading to operatively engage the threaded block means, whereby rotating the shaft acts to draw the threaded block means toward or away from the pivot block means;
   f. battery means for activating the electrical input of the motor means;
   g. control means for connecting the battery means to the electrical input of the motor means whereby the motor means may be activated in a selected direction by the user, closing or opening the jaw means.
2. The reaching aid of claim 1 in which the gripping ends of the jaw means are shaped such that at least one flat area of each jaw means contacts the other in a parallel fashion when the jaw means are in the closed position.
3. The reaching aid of claim 2 in which the arm of each jaw means is shaped such that there is a gripping area on the arm large enough to grip rounded objects between the arms when the jaw means are in a position intermediate the open and closed positions.
4. The reaching aid of claim 1 in which at least the gripping ends of the jaw means are covered with a gripping material at least in the area in which the end of one jaw means contacts the end of the other jaw means when in the closed positon.
5. The reaching aid of claim 4 in which the gripping material is closed cell foam plastic.
6. The reaching aid of claim 1 in which the handle and the body meet at such an angle that when the handle is parallel to the floor, the body extends at a convenient angle for picking up objects.
7. The reaching aid of claim 1 in which the body comprises a plurality of telescoping sections, whereby the length of the body may be adjusted by the user.

* * * * *